United States Patent
Yanagi et al.

(10) Patent No.: US 7,799,738 B2
(45) Date of Patent: Sep. 21, 2010

(54) INSECTICIDAL 2-ACYLAMINOTHIAZOLE-4-CARBOXAMIDES

(75) Inventors: Akihiko Yanagi, Tochigi (JP); Yukiyoshi Watanabe, Tochigi (JP); Jun Mihara, Tochigi (JP); Katsuhiko Shibuya, Tochigi (JP); Eiichi Shimojo, Tochigi (JP); Akira Emoto, Tochigi (JP)

(73) Assignee: Bayer CropScience AG, Monheim (DE)

( * ) Notice: Subject to any disclaimer, the term of this patent is extended or adjusted under 35 U.S.C. 154(b) by 196 days.

(21) Appl. No.: 12/091,895

(22) PCT Filed: Oct. 26, 2006

(86) PCT No.: PCT/EP2006/010315

§ 371 (c)(1), (2), (4) Date: May 22, 2008

(87) PCT Pub. No.: WO2007/051560

PCT Pub. Date: May 10, 2007

(65) Prior Publication Data

US 2008/0300136 A1    Dec. 4, 2008

(30) Foreign Application Priority Data

Oct. 31, 2005  (JP) ............................. 2005-315721

(51) Int. Cl.
- A01N 25/26 (2006.01)
- A01N 43/40 (2006.01)
- A01N 43/78 (2006.01)
- C07D 417/02 (2006.01)
- C07D 277/40 (2006.01)
- C07D 277/38 (2006.01)
- C07D 277/56 (2006.01)

(52) U.S. Cl. ....................... 504/100; 504/252; 504/266; 546/270.7; 548/194; 548/195; 548/196

(58) Field of Classification Search .................. 504/100, 504/252, 266; 546/270.7; 548/194, 195, 548/196

See application file for complete search history.

(56) References Cited

U.S. PATENT DOCUMENTS 5,981,557 A    11/1999    Nagasawa et al.

FOREIGN PATENT DOCUMENTS

| EP | 1 380 568 A2 | 1/2004 |
|---|---|---|
| EP | 1 661 886 A1 | 5/2006 |
| EP | 1 714 958 A1 | 10/2006 |
| WO | WO 2005/021488 A1 | 3/2005 |
| WO | WO 2005/030206 A1 | 4/2005 |
| WO | WO 2005/073165 A1 | 8/2005 |
| WO | WO 2005/073202 A1 | 8/2005 |

OTHER PUBLICATIONS

Feliu et al.; Synthesis of Methyl 2-Acetylamino-5-(1,3-Dithian-2-YL)Thiazole-4-Carboxylate; Heterocycles, 1997, vol. 45, No. 7, pp. 1299-1308.

Kim et al.; "The Synthesis of Aminoazole Analogs of Lysine and Arginine: The Mitsunobu Reaction With Lysinol and Arginol"; 1999; No. 8, pp. 1239-1240, New York.

*Primary Examiner*—Kamal A Saeed
*Assistant Examiner*—Kristin Bianchi
(74) *Attorney, Agent, or Firm*—Baker Donelson Bearman, Caldwell & Berkowitz, PC

(57) ABSTRACT

2-Acylaminothiazole-4-carboxamides of the formula (I) and application thereof as an insecticide.

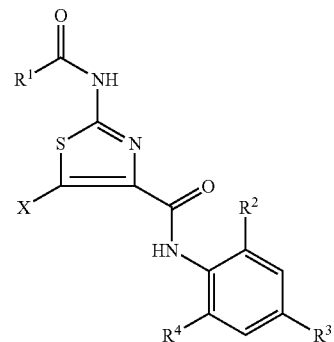

(I)

wherein $R^1$ represents phenyl which may be optionally substituted, or a 5- or 6-membered heterocyclic group containing at least one hetero atom selected from a group consisting of N, O and S which may be optionally substituted, $R^2$ represents halogen, $C_{1-6}$ alkyl or $C_{1-6}$ haloalkyl, $R^3$ represents $C_{1-6}$ haloalkyl, $C_{1-6}$ haloalkoxy, $C_{1-6}$ haloalkylthio, $C_{1-6}$ haloalkylsulfinyl or $C_{1-6}$ haloalkylsulfonyl, $R^4$ represents halogen, $C_{1-6}$ alkyl or $C_{1-6}$ haloalkyl, and X represents hydrogen, halogen, $C_{1-6}$ alkyl or $C_{1-6}$ haloalkyl, and the use of the new compounds as insecticides.

18 Claims, No Drawings

INSECTICIDAL 2-ACYLAMINOTHIAZOLE-4-CARBOXAMIDES

CROSS REFERENCE TO RELATED APPLICATIONS

This is a §371 National Stage Application of PCT/EP2006/010315 filed Oct. 26, 2006 which claims priority from JP 2005-315721 filed Oct. 31, 2005, the content of which is incorporated herein by reference.

BACKGROUND OF THE INVENTION

Field of the Invention

The present invention relates to novel 2-acylaminothiazole-4-carboxamides, their preparation their use as an insecticide and their intermediates.

Description of Related Art

It is described in the patent documents 1 and 2 that benzamides are useful as insecticides.

[Patent document 1] PCT International Publication: WO2005/021488

[Patent document 2] PCT International Publication: WO2005/073165

SUMMARY OF THE INVENTION

There have now been found novel 2-acylaminothiazole-4-carboxamides of the formula (I)

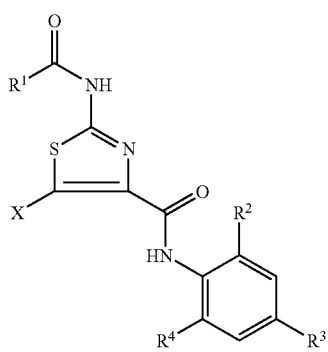

(I)

wherein $R^1$ represents phenyl which may be optionally substituted, or a 5- or 6-membered heterocyclic group containing at least one hetero atom selected from a group consisting of N, O and S which may be optionally substituted, $R^2$ represents halogen, $C_{1-6}$ alkyl or $C_{1-6}$ haloalkyl, $R^3$ represents $C_{1-6}$ haloalkyl, $C_{1-6}$ haloalkoxy, $C_{1-6}$ haloalkylthio, $C_{1-6}$ haloalkylsulfinyl or $C_{1-6}$ haloalkylsulfonyl, $R^4$ represents halogen, $C_{1-6}$ alkyl or $C_{1-6}$ haloalkyl, and X represents hydrogen, halogen, $C_{1-6}$ alkyl or $C_{1-6}$ haloalkyl.

DETAILED DESCRIPTION OF A PREFERRED EMBODIMENT

The compounds of the formula (I), according to the present invention, can be obtained, for example, by the following preparation methods (a) and (b);

Preparation Method (a):

A method of reacting compounds of the formula (II)

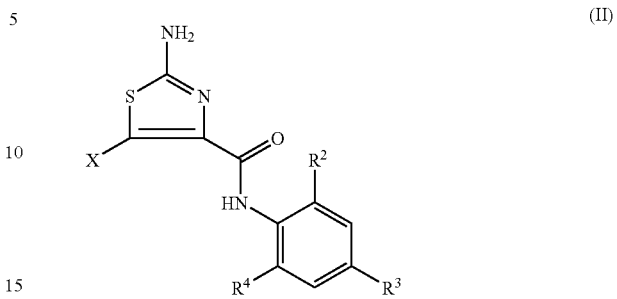

(II)

wherein $R^2$, $R^3$, $R^4$ and X are as defined above, with compounds of the formula (III)

(III)

wherein $R^1$ is as defined above and Hal represents halogen, in the presence of inert solvents, and if appropriate, in the presence of a base and/or a phase transfer catalyst, Preparation Method (b):

A method of reacting compounds of the formula (IV)

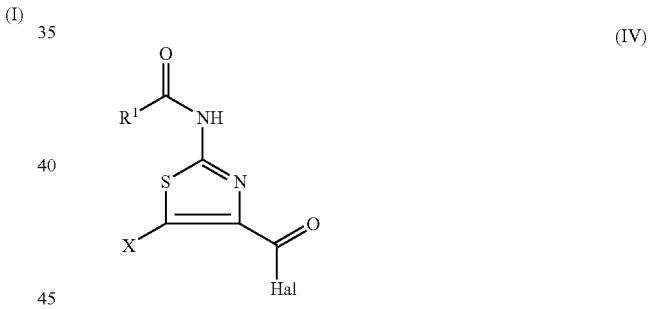

(IV)

wherein $R^1$, X and Hal are as defined above, with compounds of the formula (V)

(V)

wherein $R^2$, $R^3$ and $R^4$ are as defined above, in the presence of inert solvents, and if appropriate, in the presence of a base and/or a phase transfer catalyst.

According to the present invention, 2-acylaminothiazole-4-carboxamides of the formula (I) exhibit strong insecticidal action.

The compounds of the formula (I) of the present invention surprisingly exhibits particularly remarkable insecticidal action in comparison with a compound having a structure similar—to the compounds of the present invention.

In the specification, "halogen" represents fluorine, chlorine, bromine and iodine and represents preferably fluoro, chloro, bromo and iodo.

Examples of "alkyl" include linear or branched $C_{1-12}$ alkyl such as methyl, ethyl, n- or iso-propyl, n-, iso-, sec- or tert-butyl, n-pentyl, n-hexyl, n-heptyl, n-octyl, n-nonyl, n-decyl, n-undecyl and n-dodecyl, and preferably $C_{1-6}$ alkyl.

Each of alkyl portions in the "haloalkyl", "haloalkoxy", "haloalkylthio", "haloalkylsulfinyl", "haloalkylsulfonyl", "alkoxy", "alkylthio", "alkylsulfinyl" and "alkylsulfonyl" can include those similar to those as illustrated above for the "alkyl".

Each of halogen portions in the "haloalkyl", "haloalkoxy", "haloalkylthio", "haloalkylsulfinyl", "haloalkylsulfonyl", can include those similar to those as illustrated above for the "halogen".

The "5- or 6-membered heterocyclic group" contains at least one hetero atom selected from a group consisting of N, O and S, and examples thereof can include thienyl, furyl, pyrazolyl, imidazolyl, oxazolyl, isoxazolyl, thiadiazolyl, triazolyl, oxadiazolyl, pyridyl, pyrimidinyl, pyrazinyl and triazinyl and, in particular, thienyl, furyl, pyrazolyl, isoxazolyl, thiadiazolyl, pyridyl and pyrimidinyl can be mentioned.

The compounds of the formula (I) of the present invention can preferably include those in which, $R^1$ represents phenyl which may be optionally substituted with at least one selected arbitrarily from a group consisting of $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkyl, $C_{1-6}$ haloalkoxy, $C_{1-6}$ haloalkylthio, $C_{1-6}$ haloalkylsulfinyl or $C_{1-6}$ haloalkylsulfonyl, nitro, hydroxy and halogen, or a 5- or 6-membered heterocyclic group containing at least one hetero atom selected from a group consisting of N, O and S which may be optionally substituted with at least one selected arbitrarily from a group consisting of $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkyl, $C_{1-6}$ haloalkoxy, $C_{1-6}$ haloalkylthio, $C_{1-6}$ haloalkylsulfinyl or $C_{1-6}$ haloalkylsulfonyl, nitro, hydroxy and halogen, $R^2$ represents halogen, $C_{1-4}$ alkyl or $C_{1-4}$ haloalkyl, $R^3$ represents $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl, $R^4$ represents halogen, $C_{1-4}$ alkyl or $C_{1-4}$ haloalkyl, and X represents hydrogen, halogen, $C_{1-4}$ alkyl or $C_{1-4}$ haloalkyl.

Among these, in particular, the compounds of the formula (I) are preferably those in which, $R^1$ represents phenyl which may be optionally substituted with at least one selected arbitrarily from a group consisting of $C_{1-4}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl, nitro, hydroxy and halogen, or pyridyl, pyrazolyl, thienyl, furyl, isoxazolyl or thiadiazolyl which may be optionally substituted with at least one selected arbitrarily from a group consisting of $C_{1-4}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl, nitro, hydroxy and halogen, $R^2$ represents fluoro, chloro, bromo, iodo, methyl, ethyl, propyl, butyl, trifluoromethyl or perfluoroethyl, $R^3$ represents $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl, $R^4$ represents fluoro, chloro, bromo, iodo, methyl, ethyl, propyl, butyl, trifluoromethyl or perfluoroethyl, and X represents hydrogen, fluoro, chloro, bromo, iodo or methyl.

Among these, in very particular, the compounds of the formula (I) are preferably those in which, $R^1$ represents phenyl which may be optionally substituted with at least one selected arbitrarily from chloro and fluoro or $R^1$ represents thienyl or furyl, $R^2$ represents bromo, iodo, methyl, $R^3$ represents $C_{1-4}$ haloalkyl, $R^4$ represents bromo, iodo, methyl, ethyl, and X represents hydrogen or chloro.

The above-mentioned preparation method (a) can be represented by the following reaction formula when, for example, 2-amino-N-(2,6-dimethyl-4-heptafluoroisopropylphenyl)-1,3-thiazole-4-carboxamide and benzoyl chloride are used as starting materials.

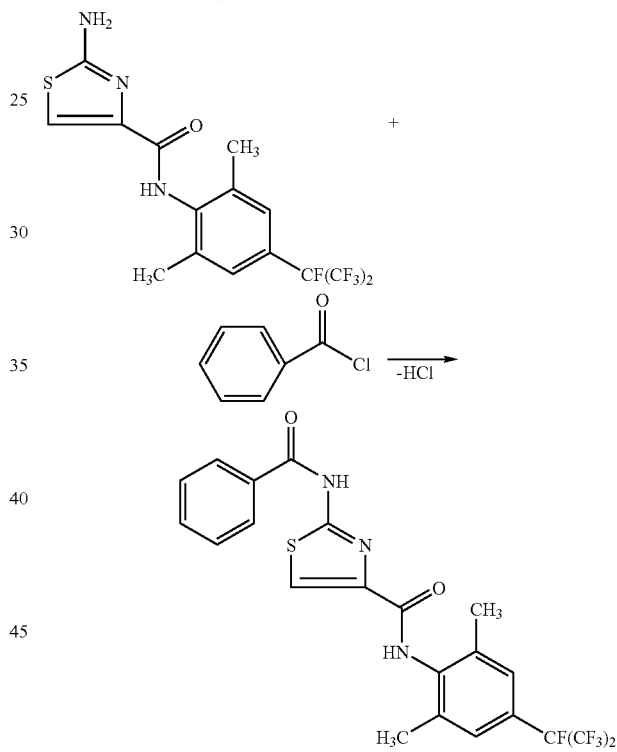

The above-mentioned preparation method (b) can be represented by the following reaction formula when, for example, 2-[(2-chlorobenzoyl)amino]-1,3-thiazole-4-carbonyl chloride and 2,6-dimethyl-4-heptafluoroisopropylaniline are used as starting materials.

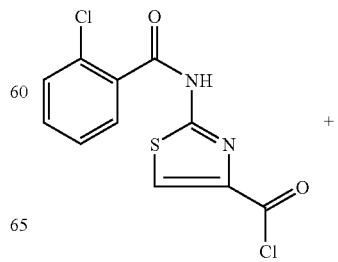

-continued

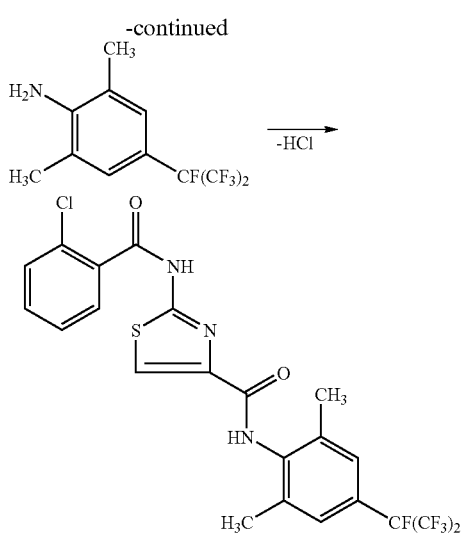

The compounds of the formula (II) which are used as a raw material in the above-mentioned preparation method (a) can be routinely obtained by the elimination reaction of tert-butoxycarbonyl from compounds of the formula (VI)

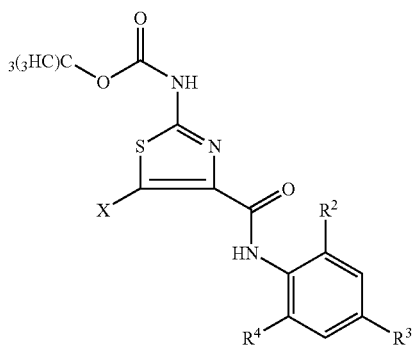

wherein $R^2$, $R^3$, $R^4$ and X are as defined above.

The compounds of the formula (VI) are easily obtained using compounds of the formula (IX) hereinafter as a starting material as shown by a later-mentioned representative Example.

As the typical examples of the compounds of the formula (VI), the following compounds can be exemplified. 2-(tert-butoxycarbonylamino)-N-(2,6-dimethyl-4-heptafluoroisopropylphenyl)-1,3-thiazole-4-carboxamide and 2-(tert-butoxycarbonylamino)-N-(2-ethyl-6-methyl-4-heptafluoroisopropylphenyl)-1,3-thiazole-4-carboxamide.

As the typical examples of the compounds of the formula (II), the following compounds can be exemplified.
2-Amino-N-(2,6-dimethyl-4-heptafluoroisopropylphenyl)-1,3-thiazole-4-carboxamide and
2-Amino-N-(2-ethyl-6-methyl-4-heptafluoroisopropylphenyl)-1,3-thiazole-4-carboxamide.

The compounds of the formula (III) being a raw material in the preparation method (a) are known compounds and are commercially available. Alternatively, it can be easily synthesized from a corresponding known carboxylic acid according to a usual method.

Specific examples thereof include benzoyl chloride, 2-chlorobenzoyl chloride, 3-chlorobenzoyl chloride, 4-chlorobenzoyl chloride, 2-fluorobenzoyl chloride, 3-fluorobenzoyl chloride, 4-fluorobenzoyl chloride, 2,3-dichlorobenzoyl chloride, 2,4-dichlorobenzoyl chloride, 2,6-dichlorobenzoyl chloride, 2,3-difluorobenzoyl chloride, 2,4-difluorobenzoyl chloride, 2,6-difluorobenzoyl chloride, nicotinyl chloride, 4-trifluormethylnicotinyl chloride, 6-chloronicotinyl chloride, 6-fluoronicotinyl chloride, 2-fluoronicotinyl chloride, 2-chloronicotinyl chloride, 2-bromonicotinyl chloride, 2,6-difluoronicotinyl chloride, 4-chloropicolinoyl chloride, 2-chloroisonicotinyl chloride, thiophene-3-carbonyl chloride, 2,5-dichlorothiophene-3-carbonyl chloride, thiophene-2-carbonyl chloride, 3-chlorothiophene-2-carbonyl chloride, 3-(t-butyl)-1-methylpyrazole-5-carbonyl chloride, 4-methyl-1,2,3-thiadiazole-5-carbonyl chloride, 2-furoyl chloride and the like.

The reaction of the above-mentioned preparation method (a) can be carried out in an appropriate diluent and examples of the diluent used include aliphatic, alicyclic and aromatic hydrocarbons which may be occasionally chlorinated, such as, pentane, hexane, cyclohexane, petroleum ether, benzene, toluene, xylene, dichloromethane and dichloroethane; ethers such as, ethyl ether, methyl ethyl ether, isopropyl ether, butyl ether, dioxane, dimethoxyethane (DME), tetrahydrofuran (THF) and diethyleneglycoldimethyl ether (DGM); ketones such as, acetone, methyl ethyl ketone (MEK), methyl isopropyl ketone, methyl isobutyl ketone (MIBK); nitriles such as, acetonitrile, propionitrile and acrylonitrile; esters such as, ethyl acetate, amyl acetate and the like.

The preparation method (a) can be carried out in the presence of a base. The base includes inorganic bases such as hydroxide, carbonate, bicarbonate and the like of an alkali metal, for example, sodium hydrogencarbonate, potassium hydrogencarbonate, sodium carbonate, potassium carbonate, lithium hydroxide, sodium hydroxide, potassium hydroxide and the like; and organic bases such as tertiary amines, dialkylaminoanilines and pyridines, for example, triethylamine, 1,1,4,4-tetramethyletheylenediamine (TMEDA), N,N-dimethylaniline, N,N-diethylaniline, pyridine, 4-dimethylaminopyridine (DMAP), 1,4-diazabicyclo[2.2.2]octane (DABCO) and 1,8-diazabicyclo[5.4.0]undec-7-ene (DBU) and the like.

The above-mentioned preparation method (a) can be carried out using a phase transfer catalyst. Examples of the diluent used include water; aliphatic, alicyclic and aromatic hydrocarbons which may be occasionally chlorinated, such as, pentane, hexane, cyclohexane, benzene, toluene and xylene; ethers such as, ethyl ether, methyl ethyl ether, methyl butyl ether, isopropyl ether and butyl ether.

Examples of the phase transfer catalyst include quaternary ions such as, tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; crown ethers such as, dibenzo-18-crown-6, dicyclohexyl-18-crown-6 and 18-crown-6; cryptands such as, [2.2.2]-cryptate, [2.1.1]-cryptate, [2.2.1]-cryptate, [2.2.B]-cryptate, [2O2O2S]-cryptate and [3.2.2]-cryptate, and the like.

The preparation method (a) can be carried out within a substantially wide range of temperature and can be generally carried out at about −40 to about 200° C. and preferably about −20 to about 150° C. Further, the reaction is desirably carried out under normal pressure but can be also operated under pressure or under reduced pressure.

When the preparation method (a) is carried out, the aimed compounds can be obtained by reacting, for example, 1 mol or slightly excessive amount of the compounds of formula (III) with 1 mol of the compounds of formula (II) in the presence of pyridine in a diluent, for example, THF.

The compounds of formula (IV) used as a raw material in the preparation method (b) include known compounds and typical example thereof includes 2-[(2-fluorobenzoyl)amino]-1,3-thiazole-4-carbonyl chloride, 2-[(3-fluorobenzoyl)amino]-1,3-thiazole-4-carbonyl chloride, 2-[(4-fluorobenzoyl)amino]-1,3-thiazole-4-carbonyl chloride, 2-[(3-trifluoromethylbenzoyl)amino]-1,3-thiazole-4-carbonyl chloride, 2-[(2-chlorobenzoyl)amino]-1,3-thiazole-4-carbonyl chloride, 2-[(4-chlorobenzoyl)amino]-1,3-thiazole-4-carbonyl chloride, 2-[(2,4-dichlorobenzoyl)amino]-1,3-thiazole-4-carbonyl chloride, 2-[(2,5-dichlorobenzoyl)amino]-1,3-thiazole-4-carbonyl chloride and the like.

The compounds of the above formula (IV) can be easily obtained by halogenating compound of the following formula (VII)

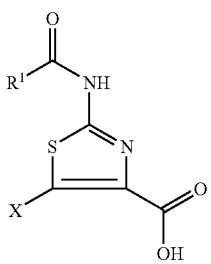

(VII)

wherein $R^1$ and X are as defined above.

The typical examples of the compounds of the formula (VII) include 2-(benzoylamino)-1,3-thiazole-4-carboxylic acid, 2-[(2-fluorobenzoyl)amino]-1,3-thiazole-4-carboxylic acid, 2-[(3-fluorobenzoyl)amino]-1,3-thiazole-4-carboxylic acid, 2-[(4-fluorobenzoyl)amino]-1,3-thiazole-4-carboxylic acid, 2-[(3-trifluoromethylbenzoyl)amino]-1,3-thiazole-4-carboxylic acid, 2-[(2-chlorobenzoyl)amino]-1,3-thiazole-4-carboxylic acid, 2-[(4-chlorobenzoyl)amino]-1,3-thiazole-4-carboxylic acid, 2-[(2,4-dichlorobenzoyl)amino]-1,3-thiazole-4-carboxylic acid, 2-[(2,5-dichlorobenzoyl)amino]-1,3-thiazole-4-carboxylic acid and the like.

The compounds of the formula (VII) can be easily obtained by hydrolyzing compounds of the following formula (VIII) according to the usual method

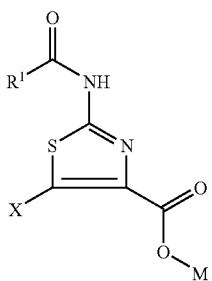

(VIII)

wherein $R^1$ and X are as defined above, and M represents $C_{1-4}$ alkyl.

The typical examples of the compounds of formula (VIII) include ethyl 2-(benzoylamino)-1,3-thiazole-4-carboxylate, ethyl 2-[(3-fluorobenzoyl)amino]-1,3-thiazole-4-carboxylate, ethyl 2-[(4-fluorobenzoyl)amino]-1,3-thiazole-4-carboxylate, ethyl 2-[(3-trifluoromethylbenzoyl)amino]-1,3-thiazole-4-carboxylate, ethyl 2-[(2-fluorobenzoyl)amino]-1,3-thiazole-4-carboxylate, ethyl 2-[(2-chlorobenzoyl)amino]-1,3-thiazole-4-carboxylate, ethyl 2-[(4-chlorobenzoyl)amino]-1,3-thiazole-4-carboxylate, ethyl 2-[(2,4-dichlorobenzoyl)amino]-1,3-thiazole-4-carboxylate, ethyl 2-[(2,5-dichlorobenzoyl)amino]-1,3-thiazole-4-carboxylate, ethyl 2-[(3,4-dichlorobenzoyl)amino]-1,3-thiazole-4-carboxylate, ethyl 2-[(2-thienylcarbonyl)amino]-1,3-thiazole-4-carboxylate, ethyl 2-[(2-furanylcarbonyl)amino]-1,3-thiazole-4-carboxylate and the like.

The compounds of the formula (VIII) can be easily obtained by reacting compounds of the following formula (IX) with the compounds of the formula (III)

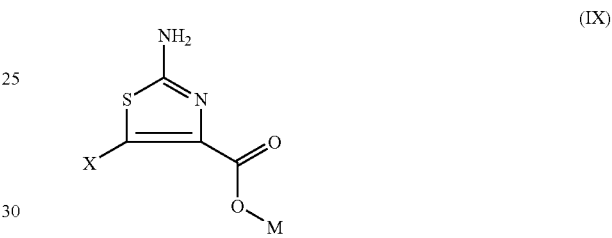

(IX)

wherein X and M are as defined above.

The typical examples of the compounds of the formula (IX) include methyl 2-aminothiazole-4-carboxylate and ethyl 2-aminothiazole-4-carboxylate.

The compounds of the formula (IX) are known compounds described in Heterocycles, Vol. 45, pages 1299 to 1308 (1997) and Synlett., Vol. 8, pages 1239 to 1240 (1999).

The compounds of the formula (V) which are another raw material in the preparation method (b) are known compounds described in EP1380568 or WO 2005/021488 and can be easily obtained in accordance with the method described in these publications. Typical examples include 2,6-dimethyl-4-pentafluoroethylaniline, 2,6-dimethyl-4-heptafluoroisopropylaniline, 2-ethyl-4-heptafluoroisopropyl-6-methylaniline, 2,6-diethyl-4-heptafluoroisopropylaniline, 2,6-dichloro-4-heptafluoroisopropylaniline, 2,6-dimethyl-4-heptafluoro-n-propylthioaniline, 2,6-dichloro-4-heptafluoro-n-propylthioaniline and the like.

A series of reaction scheme related to the above-mentioned preparation method (b) are as follows.

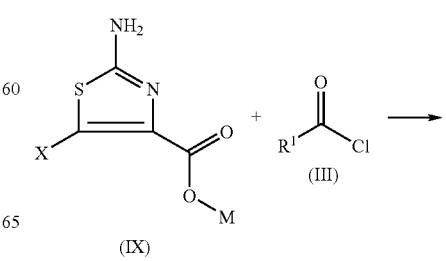

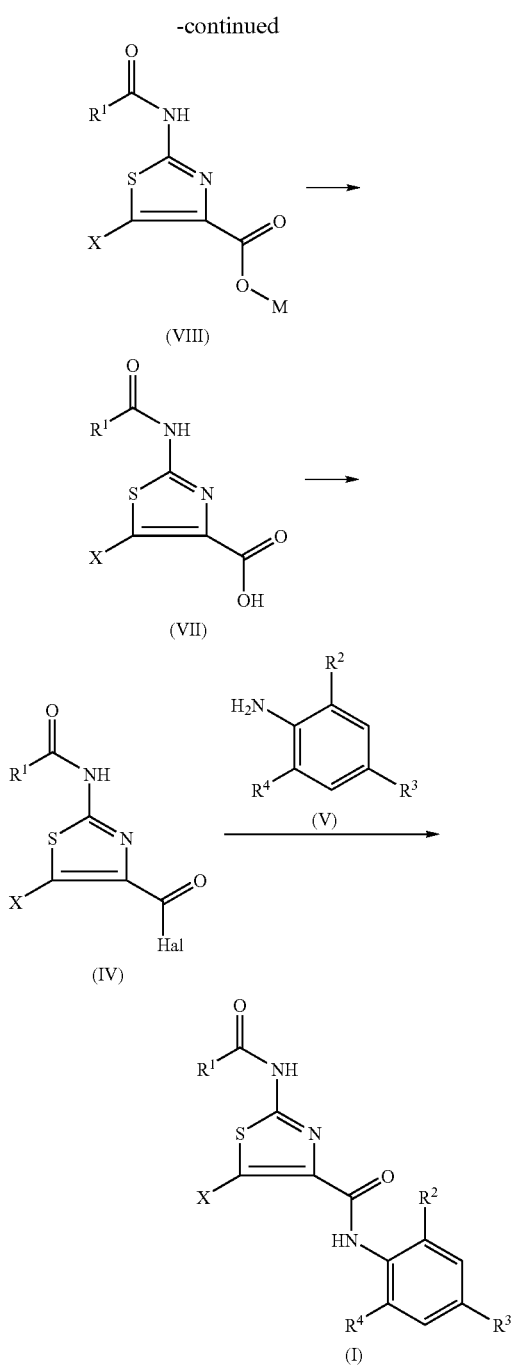

In the above reaction scheme, the reaction of the compounds of the formula (IX) with the compounds of the formula (III) can be carried out in an appropriate diluent. Examples of the diluent used include aliphatic, alicyclic and aromatic hydrocarbons which maybe occasionally chlorinated, such as, pentane, hexane, cyclohexane, petroleum ether, benzene, toluene, xylene, dichloromethane and dichloroethane; ethers such as, ethyl ether, methyl ethyl ether, isopropyl ether, butyl ether, dioxane, dimethoxyethane (DME), tetrahydrofuran (THF) and diethylene glycol dimethyl ether (DGM); ketones such as, acetone, methyl ethyl ketone (MEK), methyl isopropyl ketone, methyl isobutyl ketone (MIBK); nitriles such as, acetonitrile, propionitrile and acrylonitrile; esters such as, ethyl acetate, amyl acetate and the like.

The above-mentioned reaction can be carried out in the presence of a base. Acid binding agent used as the base includes inorganic bases such as hydroxide, carbonate, bicarbonate and the like of an alkali metal, for example sodium hydrogencarbonate, potassium hydrogencarbonate, sodium carbonate, potassium carbonate, lithium hydroxide, sodium hydroxide, potassium hydroxide and the like; and organic bases such as alcoholate, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2.2.2]octane (DABCO) and 1,8-diazabicyclo[5.4.0]undec-7-ene (DBU) and the like.

The above-mentioned reaction can be carried out using a phase transfer catalyst. Examples of the diluent used include water; aliphatic, alicyclic and aromatic hydrocarbons which may be occasionally chlorinated, such as, pentane, hexane, cyclohexane, benzene, toluene and xylene; ethers such as, ethyl ether, methyl ethyl ether, methyl butyl ether, isopropyl ether and butyl ether.

Examples of the phase transfer catalyst include quaternary ions such as, tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; crown ethers such as, dibenzo-18-crown-6, dicyclohexyl-18-crown-6 and 18-crown-6; cryptands such as, [2.2.2]-cryptate, [2.1.1]-cryptate, [2.2.1]-cryptate, [2.2.B-]-cryptate, [2O2O2S]-cryptate and [3.2.2]-cryptate, and the like.

The above-mentioned reaction can be carried out within a substantially wide range of temperature and can be generally carried but at about −40 to about 200° C. and preferably about −20 to about 110° C. Further, the reaction is desirably carried out under normal pressure but can be also operated under pressure or under reduced pressure.

When the reaction is carried out, the aimed compounds can be obtained by reacting, for example, 1 mol or slightly excessive amount of the compounds of the formula (III) with 1 mol of the compounds of the formula (IX) in the presence of pyridine in a diluent, for example, THF.

The preparation method of the compounds of the formula (VII) by hydrolysis of the compounds of the formula (VIII) can be carried out in an appropriate diluent. Examples of the diluent used include water; ethers such as, ethyl ether, methyl ethyl ether, isopropyl ether and butyl ether, dioxane, tetrahydrofuran (THF); alcohols such as, methanol, ethanol, isopropanol, butanol, ethylene glycol and the like.

The above-mentioned reaction is carried out using the hydroxide of an alkali metal or alkaline earth metal as inorganic bases, such as, sodium hydroxide, potassium hydroxide, calcium hydroxide; and hydrochloric acid and sulfuric acid and the like as inorganic acids.

The above-mentioned reaction can be carried out within a substantially wide range of temperature and can be generally carried out at about 0 to about 20° C. and preferably about room temperature to about 150° C. Further, the reaction is desirably carried out under normal pressure but can be also operated under pressure or under reduced pressure.

When the above-mentioned reaction is carried out, the aimed compounds of the formula (VII) can be obtained by reacting potassium hydroxide with 1 mol of the compounds of the formula (VIII) in a diluent such as a mixed solvent of ethanol and water.

Further, the preparation method of obtaining the compounds of the formula (IV) from the compounds of the formula (VII) can be carried out in an appropriate diluent. Examples of the diluent used include aliphatic, alicyclic and aromatic hydrocarbons which may be occasionally chlorinated, such as, hexane, cyclohexane, benzene, toluene, xylene, chlorobenzene, dichloromethane and dichloroethane.

The above-mentioned reaction can be carried out by using thionyl chloride and thionyl bromide and the like as a halogenation agent and adding DMF and the like as a catalyst.

The above-mentioned reaction can be carried out within a substantially wide range of temperature and can be generally carried out at about 0 to about 200° C. and preferably about room temperature to about 150° C. Further, the reaction is desirably carried out under normal pressure but can be also operated under pressure or under reduced pressure.

When the above-mentioned reaction is carried out, the aimed compounds of the formula (IV) can be obtained by adding a catalytic amount of DMF to 1 mol of the compounds of the formula (VII) in a diluent, for example, 1,2-dichloroethane and then by reacting the compounds with thionyl chloride.

The preparation method (b) of the final reaction of the above-mentioned scheme can be carried out in an appropriate diluent. Examples of the diluent used include aliphatic, alicyclic and aromatic hydrocarbons which may be occasionally chlorinated, such as, pentane, hexane, cyclohexane, petroleum ether, ligroin, benzene, toluene, xylene, dichloromethane and dichloroethane; ethers such as, ethyl ether, methyl ethyl ether, isopropyl ether, butyl ether, dioxane, dimethoxyethane (DME), tetrahydrofuran (THF) and diethylene glycol dimethyl ether (DGM); ketones such as, acetone, methyl ethyl ketone (MEK), methyl isopropyl ketone, methyl isobutyl ketone (MIBK); nitriles such as, acetonitrile, propionitrile and acrylonitrile; esters such as, ethyl acetate, amyl acetate and pyridine and the like.

The preparation method (b) can be carried out in the presence of a base. Acid binding agent used as the base includes inorganic bases such as hydroxide, carbonate, bicarbonate and the like of an alkali metal, for example, sodium hydrogencarbonate, potassium hydrogencarbonate, sodium carbonate, potassium carbonate, lithium hydroxide, sodium hydroxide, potassium hydroxide and the like; and organic bases such as tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2.2.2]octane (DABCO) and 1,8-diazabicyclo[5.4.0]undec-7-ene (DBU) and the like.

The above-mentioned preparation method (b) can also be carried out using a phase transfer catalyst. Examples of the diluent used include water; aliphatic, alicyclic and aromatic hydrocarbons which may be occasionally chlorinated, such as, pentane, hexane, cyclohexane, benzene, toluene and xylene; ethers such as, ethyl ether, methyl ethyl ether, methyl butyl ether, isopropyl ether and butyl ether.

Examples of the phase transfer catalyst include quaternary ions such as, tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; crown ethers such as, dibenzo-18-crown-6, dicyclohexyl-18-crown-6 and 18-crown-6; cryptands such as, [2.2.2]-cryptate, [2.1.1]-cryptate, [2.2.1]-cryptate, [2.2.B]-cryptate, [2O2O2S]-cryptate and [3.2.2]-cryptate, and the like.

The preparation method (b) can be carried out within a substantially wide range of temperature and can be generally carried out at about −40 to about 200° C. and preferably about −20 to about 150° C. Further, the reaction is desirably carried out under normal pressure but can be also operated under pressure or under reduced pressure.

When the preparation method (b) is carried out, the aimed compounds can be obtained by reacting, for example, 1 mol or slightly excessive amount of the compounds of the formula (V) with 1 mol of the compounds of the formula (IV) in a diluent, for example, pyridine.

The compounds of the formula (I) of the present invention exhibits strong insecticidal action. Accordingly, the compounds of the formula (I) of the present invention can be used as an insecticide. Further, the active compounds of the formula (I) of the present invention do not impart harmful effects against cultivated plants and exhibits accurate pest control effect against harmful insects. Further, the compounds of the present invention can be used for pest control of harmful juice absorbing insects, chewing insects and other plant parasitic harmful insects, storing harmful insects, insanitary insects and the like and can be applied for extirpation and eradication.

As examples of the harmful insects, the following harmful insects can be exemplified.

The insects include Coleoptera harmful insects such as, *Callosobruchus Chinensis, Sitophilus zeamais, Tribolium castaneum, Epilachnavigintioctomaculata, Agriotes fuscicollis, Anomala rufocuprea, Leptinotarsa decemlineata, Diabrotica* spp., *Monochamus alternatus, Lissorhoptrus oryzophilus* and *Lyctus bruneus*; Lepidoptera harmful insects such as, *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotisfucosa, Galleria mellonella, Plutella maculipennis, Heliothis virescens* and *Phyliocnistis citrella*; Hemiptera harmful insects such as, *Nephotettix cincticeps, Nilaparvata lugens, Pseudococcus comstocki, Unaspis yanonensis, Myzus persicas, Aphis pomi, Aphis gossypii, Phopalosiphum pseudobrassicas, Stephanitis nashi, Nazara* spp., *Trialeurodes vaporariorm* and *Pshylla* spp.; Thysanoptera harmful insects such as, *Thrips palmi* and *Franklinella occidental*; Orthoptera harmful insects such as, *Blatella germanica, Periplaneta americana, Gryllotalpa africana* and *Locusta migratoria* migratoriaodes; Isoptera harmful insects such as, *Reticulitermes speratus* and *Coptotermes formosanus*; Diptera harmful insects such as, *Musca domestica, Aedes aegypti, Hylemia platura, Culex pipiens, Anopheles slnensis, Culex tritaeniorhychus* and *Liriomyza trifolii*, and the like.

Further, examples of mites include *Tetranychus cinnabarinus, Tetranychus urticae, Panonychus citri, Aculops pelekassi, Tarsonemus* Spp. and the like.

Further, examples of nematodes include *Meloidogyne incognita, Bursaphelenchus lignicolus Mamiya et Kiyohara, Aphelenchoides besseyi, Heterodera glycines, Pratylenchus* spp. and the like.

Further, in the field of animal medicine, the novel compounds of the present invention can be effectively used for various harmful animal parasite worms (internal or external parasite), for example, insects and worms.

As examples of the animal parasite worm, the following harmful insects can be exemplified.

Examples of insects include *Gastrophilus* spp., *Stomoxys* spp., *Trichodectes* spp., *Rhodnius* spp., Ctenocephalidescanis, *Cimx lecturius* and the like.

Examples of mites include *Ornithodoros* spp., *Ixodes* spp., *Boophilus* spp. and the like.

In the present invention, a substance having insecticidal action for harmful insects including all of these is occasionally called as an insecticide.

When the active compounds of the present invention is used as an insecticide, usual formulation form can be made. Examples of the formulation form include liquid, emulsion, water-dispersible agent, water-dispersible granular formulation, suspension, powder, foam, paste, tablets, granules, aerosol, the infiltration of an active compound-natural and synthetic, microcapsules, coating agents for seeds, formulations with a combusting device (as the combusting device, for example, a fumigation and fume cartridge, a can, a coil and the like), ULV [cold mist, warm mist] and the like.

These formulations can be produced by known methods. For example, they can be produced by mixing the active compound with an extending agent, namely, liquid diluent or carrier; liquified gas diluent or carrier; solid diluent or carrier, in some cases, together with a surfactant, namely, an emulsifier and/or a dispersant and/or a foam forming agent.

When water is used as the extending agent, for example, an organic solvent can be used as a solvent aid.

Examples of liquid diluent or carrier include aromatic hydrocarbons, for example, xylene, toluene, alkylnaphthalene and the like, chlorinated aromatic or chlorinated aliphatic hydrocarbons, for example, chlorobenzenes, ethylene chlorides, methylene chlorides, aliphatic hydrocarbons, for example, cyclohexanes, paraffins such as fractions of mineral oil, alcohols, for example, butanol, glycol and ether thereof, ester thereof and the like, ketones, for example, acetone, methyl ethyl ketone, methyl isobutyl ketone, cyclohexanone and the like, strong polar solvents, for example, dimethylformamide, dimethylsulfoxide and the like, water and the like.

Liquified gas diluent or carrier includes those which are gas at normal temperature and pressure, for example, aerosol injection agents such as butane, propane, nitrogen gas, carbon dioxide and halogenated hydrocarbons.

Examples of solid diluent include pulverized natural minerals, for example, kaolin, clay, talc, choke, silica, attapulgite, montmorillonite or diatomaceous earth and the like, pulverized synthetic minerals, for example, highly dispersed silicic acid, alumina, silicate and the like.

Examples of solid carrier for granules include pulverized and fractionated rocks, for example, calcite, marble, pumice, sea-foam, dolomite and the like, synthesized granules of inorganic or organic powder, fine granules of organic substances, for example, sawdust, husks of coconut, cobs of corn, stalks of tobacco and the like.

Examples of emulsifying agent and/or foaming agent include nonionic and anionic surfactants, for example, polyoxyethylene, aliphatic acid ester, polyoxyethylene aliphatic acid alcohol ether, for example, alkylarylpolyglycol ether, alkyl sulfonate, alkyl sulfate, aryl sulfonate and the like, albumin hydrolysis product and the like.

Examples of dispersant include lignin sulfite waste fluid and methyl cellulose.

A fixing agent can be used for formulations of powder, granules or emulsion, and examples of the fixing agent include carboxymethyl cellulose, natural or synthetic polymer, such as gum arabic, polyvinyl alcohol, polyvinyl acetate and the like.

A coloring agent can also be used and examples of the coloring agent include inorganic pigments such as iron oxide, titanium oxide, Prussian blue and the like, organic dyes such as alizarin dye, azo dye or metal phthalocyanine dye, and further, trace amount of elements such as salts of iron, manganese, boron, copper, cobalt, molybdenum and zinc.

The formulations can contain the active component by an amount within a range of 0.1 to 95% by weight and preferably 0.5 to 90% by weight.

The active compounds of the formula (I) of the present invention in commercially useful formulation and in use form prepared from those formulations can also exist as a mixture with other active compounds such as, an insecticide, poison food, a bactericidal, an acaricidal agent, a nematicidal agent, a fungicide, a growth control agent and a herbicide. Examples of the above-mentioned insecticide include an organophosphorus pesticide, a carbamate agent, a carboxylate base agent, a chlorinated hydrocarbon base agent, an insecticidal substance produced by microbe and the like.

Further, the active compounds of the formula (I) of the present invention can also exist as an admixture with a synergistic agent and its formulation and use form include those which are commercially useful. The synergistic agent itself is not required to be active and is a compound reinforcing the action of the active compound.

The content of the active compounds of the formula (I) of the present invention in the industrially useful use form can vary within a wide range.

The concentration of the active compounds of the formula (I) of the present invention in practical use can be, for example, within a range of 0.0000001 to 100% by weight and preferably 0.00001 to 1% by weight.

The active compounds of the formula (I) of the present invention can be used in the usual manner suitable for the use from.

The active compounds of the present invention has stability for alkali on a caustic lime substance when it is used for insanitary insects and harmful insects for a preservation article and further, exhibits excellent residual effectiveness in timbers and land.

Now, the present invention is more specifically illustrated by Examples but it is not intended that the present invention is limited thereto.

SYNTHESIS EXAMPLE 1
Starting Raw Material

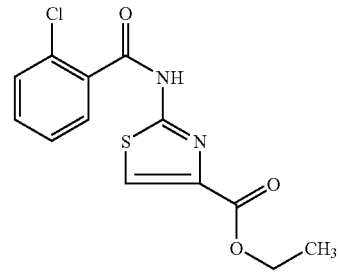

1.07 g of o-chlorobenzoyl chloride was added to a solution in which 1.00 g of ethyl 2-amino-1,3-thiazole-4-carboxylate and 0.69 g of pyridine were dissolved in THF, under ice cooling. Then, after the reaction mixture was stirred at room temperature for 1 hr, it was poured into water and extracted with ethyl acetate. The organic layer was washed with an aqueous 2N-hydrochloric acid solution and dried on anhydrous magnesium sulfate. After distilling off the solvent, the crude product obtained was washed with a mixed solvent of hexane and t-butyl methyl ether to obtain 1.52 g of the aimed ethyl 2-(2-chlorobenzoyl)amino-1,3-thiazole-4-carboxylate.

$^1$H NMR (300 MHz, CDCl$_3$) δ 7.89 (1H, s), 7.83 (1H d, J=7.2), 7.35-7.55 (4H m), 4.38 (2H, q, J=7.2 Hz), 1.40 (3H, t, J=7.2 Hz).

SYNTHESIS EXAMPLE 2
Intermediate

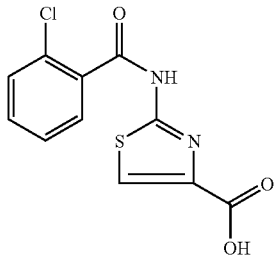

A mixture of 1.52 g of ethyl 2-(2-chlorobenzoyl)amino-1,3-thiazole-4-carboxylate, 0.68 g of potassium hydroxide, 1.8 mL of water and 9 mL of ethanol was stirred at room temperature for 4 hrs. After the reaction mixture was diluted with water, it was washed with ethyl acetate. The separated aqueous phase was acidified with an aqueous 2N-hydrochloric acid solution and the precipitated crude product was washed with water and dried to obtain 0.96 g of the aimed 2-(2-chlorobenzoyl)amino-1,3-thiazole-4-carboxylic acid.

$^1$H NMR (300 MHz, DMSO-d$_6$) δ 13.0 (2H, br s), 8.08 (1H s), 7.40-7.70 (5H m).

SYNTHESIS EXAMPLE 3
Intermediate

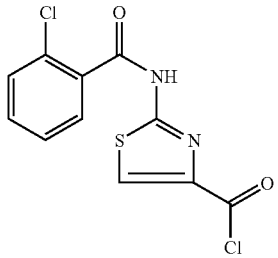

One drop of DMF was added to the toluene solution of 0.63 g of 2-(2-chlorobenzoyl)amino-1,3-thiazole-4-carboxylic acid at room temperature, and further, 0.53 g of thionyl chloride was added to be reacted at 80° C. for 6 hrs. After distilling off the solvent, the crude product of 2-(2-chlorobenzoyl)amino-1,3-thiazole-4-carbonyl chloride was used for the next step without purification.

SYNTHESIS EXAMPLE 4
Final Product

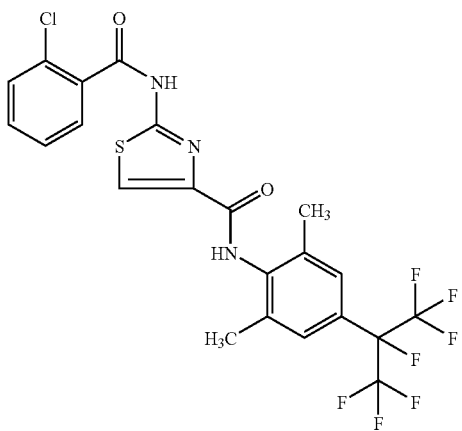

0.56 g of 2-(2-chlorobenzoyl)amino-1,3-thiazole-4-carbonyl chloride and 0.57 g of 2,6-dimethyl-4-heptafluoroisopropylaniline were dissolved in pyridine. The reaction solution was heated to reflux for 6 hrs. After completion of the reaction, it was poured into water and extracted with ethyl acetate. After the organic layer was washed with an aqueous 2N-hydrochloric acid solution, it was dried over anhydrous magnesium sulfate. After distillation of the solvent under reduced pressure, the residue obtained was purified with silica gel column chromatography using a mixed solvent of n-hexane and ethyl acetate to obtain 0.46 g of the aimed 2-(2-chlorobenzoyl)amino-N-(2,6-dimethyl-4 heptafluoroisopropylphenyl)-1,3-thiazole-4-carboxamide.

Melting point: 85-91° C.

SYNTHESIS EXAMPLE 5
Starting Raw Material

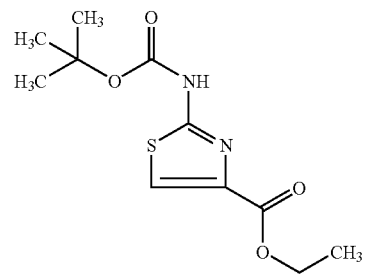

1.39 g of tert-butyl dicarbonate was added to a solution in which 1.00 g of ethyl 2-amino-1,3-thiazole-4-carboxylate, 0.88 g of triethylamine, and 0.07 g of DMAP were dissolved in THF, under ice cooling. Then, after the reaction mixture was stirred at room temperature for 1 hr, it was poured into water and extracted with ethyl acetate. The organic layer was washed with an aqueous 2N-hydrochloric acid solution and dried over anhydrous magnesium sulfate. After distilling off the solvent, the obtained crude product was washed with a mixed solvent of hexane and t-butyl methyl ether to obtain 1.5 g of the aimed ethyl 2-(tert-butoxycarbonyl)amino-1,3-thiazole-4-carboxylate.

$^1$H NMR (300 MHz, CDCl$_3$) δ 8.27 (1H, br s), 7.78 (1H s), 4.39 (2H, q, J=7.2 Hz), 1.54 (9H s), 1.39 (3H, t, J=7.2 Hz).

SYNTHESIS EXAMPLE 6
Intermediate

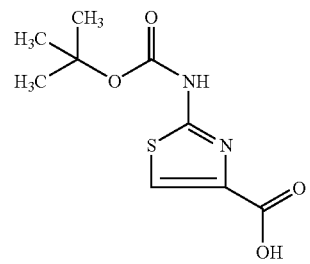

A mixture of 1.00 g of ethyl 2-(tert-butoxycarbonyl)amino-1,3-thiazole-4-carboxylate, 0.46 g of lithium hydroxide monohydrate, 10 mL of water and 10 mL of 1,4-dioxane was stirred at room temperature for 6 hrs. After the reaction mixture was diluted with water, it was washed with ethyl acetate. The separated aqueous phase was acidified with an aqueous 2N-hydrochloric acid solution and the precipitated crude product was washed with water and dried to obtain 0.82 g of the aimed 2-(tert-butoxycarbonyl)amino-1,3-thiazole-4-carboxylic acid.

$^1$H NMR (300 MHz, DMSO-d$_6$) δ 12.77 (1H, br s), 11.70 (1H, br s), 7.92 (1H s), 1.48 (9H s).

SYNTHESIS EXAMPLE 7
Intermediate

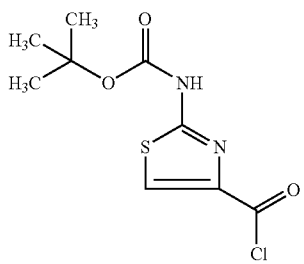

0.64 g of oxalyl chloride was added to the dichloromethane solution of 0.82 g of 2-(tert-butoxycarbonyl)amino-1,3-thiazole-4-carboxylic acid at room temperature, and further, one drop of DMF was added to be reacted at room temperature for 1 hr. Further, it was heated to reflux for 1 hr. After distilling off the solvent, the crude product of 2-(tert-butoxycarbonyl)amino-1,3-thiazole-4-carboxylic chloride was used for the next step without purification.

SYNTHESIS EXAMPLE 8
Intermediate

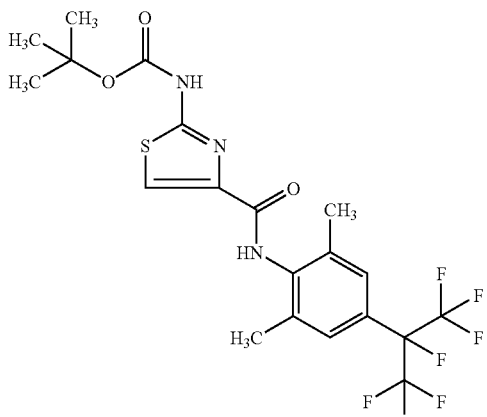

0.76 g of 2-(tert-butoxycarbonyl)amino-1,3-thiazole-4-carboxylic chloride and 0.88 g of 2,6-dimethyl-4-heptafluoroisopropylaniline were dissolved in pyridine. The reaction solution was heated to reflux for 6 hrs. After completion of the reaction, it was poured into water and was extracted with ethylacetate. After the organic phase was washed with an aqueous 2N-hydrochloric acid solution, it was dried over anhydrous magnesium sulfate. After distilling off the solvent under reduced pressure, the crude product of 2-(tert-butoxycarbonyl)amino-N-(2,6-dimethyl-4-heptafluoroisopropylphenyl)-1,3-thiazole-4-carboxamide was used for the next step without purification.

SYNTHESIS EXAMPLE 9
Intermediate

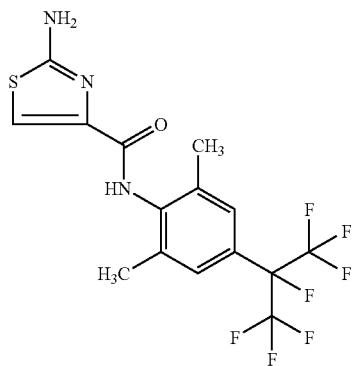

0.30 g of 2-(tert-butoxycarbonyl)amino-N-(2,6-dimethyl-4-heptafluoroisopropylphenyl)-1,3-thiazole-4-carboxamide was dissolved in trifluoroacetic acid to be reacted at room temperature for 3 hrs. The solvent was distilled off under reduced pressure, water was added and the aqueous solution was neutralized with potassium carbonate. Then, it was extracted with ethyl acetate. After the organic phase was washed with a saturated sodium chloride solution, it was dried over anhydrous magnesium sulfate. After distilling off the solvent under reduced pressure, the residue obtained was purified with silica gel column chromatography using a mixed solvent of n-hexane and ethyl acetate to obtain 0.16 g of the aimed 2-amino-N-(2,6-dimethyl-4-heptafluoroisopropylphenyl)-1,3-thiazole-4-carboxamide.

Melting point: 80-84° C.

SYNTHESIS EXAMPLE 10
Final Product

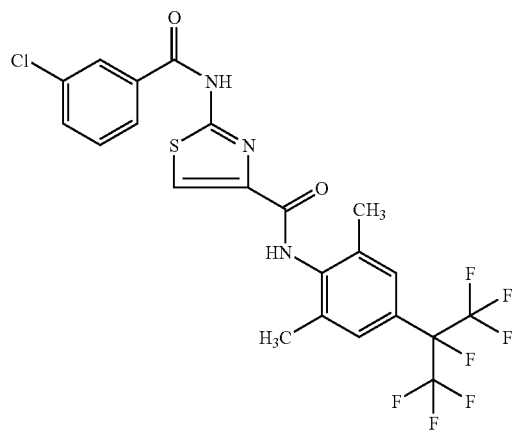

0.10 g of 2-amino-N-(2,6-dimethyl-4-heptafluoroisopropylphenyl)-1,3-thiazole-4-carboxamide was dissolved in pyridine. To the solution, 0.04 g of 3-chlorobenzoyl chloride was added and the mixture was stirred at room temperature for 6 hrs. After completion of the reaction, it was poured into water and extracted with ethylacetate. After the organic layer was washed with an aqueous 2N-hydrochloric acid solution, it was dried over anhydrous magnesium sulfate. After distilling off the solvent under reduced pressure, the residue obtained was purified with silica gel column chromatography using a mixed solvent of n-hexane and ethyl acetate to obtain 0.08 g of the aimed 2-(3-chlorobenzoyl)amino-N-(2,6-dimethyl-4-heptafluoro-isopropylphenyl)-1,3-thiazole-4-carboxamide.

Melting point: 95-100° C.

The compounds of formula (I) of the present invention which are obtained by the similar method as described in Synthetic Examples 1 to 10 are shown in Table 1. Further, the final products which were described in the above-mentioned Synthetic Examples 4 and 10 were also shown in Table 1.

TABLE 1

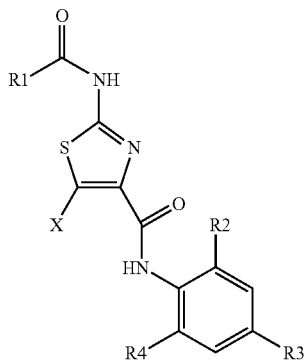

| No. | R1 | R2 | R3 | R4 | X | m. p. °C. |
|---|---|---|---|---|---|---|
| 1 | 2-(trifluoromethyl)phenyl | CH$_3$ | CF(CF$_3$)$_2$ | C$_2$H$_5$ | H | |
| 2 | 2,3-dichlorophenyl | CH$_3$ | CF(CF$_3$)$_2$ | C$_2$H$_5$ | H | |
| 3 | 2,3-dichlorophenyl | CH$_3$ | CF(CF$_3$)$_2$ | CH$_3$ | H | |
| 4 | 2,3-difluorophenyl | CH$_3$ | CF(CF$_3$)$_2$ | C$_2$H$_5$ | H | |
| 5 | 2,3-difluorophenyl | CH$_3$ | CF(CF$_3$)$_2$ | CH$_3$ | H | |
| 6 | 2,3-difluorophenyl | Br | CF(CF$_3$)$_2$ | Br | H | |
| 7 | 2,3-difluorophenyl | Cl | SO$_2$C$_2$F$_5$ | Cl | H | |
| 8 | 2,4,6-trifluorophenyl | CH$_3$ | CF(CF$_3$)$_2$ | C$_2$H$_5$ | H | |
| 9 | 2,4-dichlorophenyl | CH$_3$ | CF(CF$_3$)$_2$ | C$_2$H$_5$ | H | |
| 10 | 2,4-difluorophenyl | CH$_3$ | CF(CF$_3$)$_2$ | C$_2$H$_5$ | H | |
| 11 | 2,4-difluorophenyl | CH$_3$ | CF(CF$_3$)$_2$ | CH$_3$ | H | |
| 12 | 2,4-difluorophenyl | Cl | SO$_2$C$_3$F$_7$-n | Cl | H | |
| 13 | 2,4-difluorophenyl | CH$_3$ | SO$_2$C$_3$F$_7$-n | CH$_3$ | H | |
| 14 | 2,5-dichloro-3-thienyl | CH$_3$ | CF(CF$_3$)$_2$ | C$_2$H$_5$ | H | |
| 15 | 2,5-dichlorophenyl | CH$_3$ | CF(CF$_3$)$_2$ | C$_2$H$_5$ | H | |
| 16 | 2,5-dichlorophenyl | CH$_3$ | CF(CF$_3$)$_2$ | CH$_3$ | H | |
| 17 | 2,5-difluorophenyl | CH$_3$ | CF(CF$_3$)$_2$ | C$_2$H$_5$ | H | |
| 18 | 2,5-difluorophenyl | I | CF(CF$_3$)$_2$ | I | H | |
| 19 | 2,6-dichloro-4-pyridyl | CH$_3$ | CF(CF$_3$)$_2$ | C$_2$H$_5$ | H | |
| 20 | 2,6-dichlorophenyl | CH$_3$ | CF(CF$_3$)$_2$ | C$_2$H$_5$ | H | |
| 21 | 2,6-difluorophenyl | CH$_3$ | CF(CF$_3$)$_2$ | C$_2$H$_5$ | H | 186-188 |
| 22 | 2,6-difluorophenyl | CH$_3$ | CF(CF$_3$)$_2$ | CH$_3$ | H | |
| 23 | 2,6-difluorophenyl | C$_2$H$_5$ | CF(CF$_3$)$_2$ | C$_2$H$_5$ | H | |
| 24 | 2,6-difluorophenyl | I | CF(CF$_3$)$_2$ | I | H | 215-218 |
| 25 | 2,6-difluorophenyl | Cl | SO$_2$CF$_3$ | Cl | H | |
| 26 | 2-chloro-3-thienyl | CH$_3$ | CF(CF$_3$)$_2$ | C$_2$H$_5$ | H | |
| 27 | 2-chloro-3-pyridyl | CH$_3$ | CF(CF$_3$)$_2$ | C$_2$H$_5$ | H | |
| 28 | 2-chloro-3-pyridyl | CH$_3$ | CF(CF$_3$)$_2$ | CH$_3$ | H | |
| 29 | 2-chloro-3-pyridyl | Br | CF(CF$_3$)$_2$ | Br | H | |
| 30 | 2-chloro-4-pyridyl | CH$_3$ | CF(CF$_3$)$_2$ | C$_2$H$_5$ | H | |
| 31 | 2-chlorophenyl | CH$_3$ | CF(CF$_3$)$_2$ | I | H | |
| 32 | 2-chlorophenyl | CH$_3$ | CF(CF$_3$)$_2$ | C$_2$F$_5$ | H | |
| 33 | 2-chlorophenyl | CH$_3$ | CF(CF$_3$)$_2$ | C$_2$H$_5$ | H | |
| 34 | 2-chlorophenyl | CH$_3$ | CF(CF$_3$)$_2$ | CH$_3$ | H | 85-91 |
| 35 | 2-chlorophenyl | CH$_3$ | CF(CF$_3$)$_2$ | CH$_3$ | Cl | 202-204 |
| 36 | 2-chlorophenyl | Cl | S(O)CF$_3$ | Cl | H | |
| 37 | 2-nitrophenyl | CH$_3$ | CF(CF$_3$)$_2$ | C$_2$H$_5$ | H | |
| 38 | 2-fluoro-3-pyridyl | CH$_3$ | CF(CF$_3$)$_2$ | CH$_3$ | H | |
| 39 | 2-fluoro-3-pyridyl | CH$_3$ | CF(CF$_3$)$_2$ | C$_2$H$_5$ | H | |
| 40 | 2-fluoro-3-pyridyl | I | CF(CF$_3$)$_2$ | I | H | |
| 41 | 2-fluorophenyl | CH$_3$ | CF(CF$_3$)$_2$ | C$_2$H$_5$ | H | 171-172 |
| 42 | 2-fluorophenyl | CH$_3$ | CF(CF$_3$)$_2$ | CH$_3$ | H | 128-132 |
| 43 | 2-fluorophenyl | CH$_3$ | CF(CF$_3$)$_2$ | CH(CH$_3$)$_2$ | H | |
| 44 | 2-fluorophenyl | I | CF(CF$_3$)$_2$ | I | H | |
| 45 | 2-fluorophenyl | Br | SC$_3$F$_7$-n | Br | H | |
| 46 | 2-fluorophenyl | I | SC$_3$F$_7$-n | I | H | |
| 47 | 2-bromo-3-pyridyl | CH$_3$ | CF(CF$_3$)$_2$ | C$_2$H$_5$ | H | |
| 48 | 2-bromophenyl | CH$_3$ | CF(CF$_3$)$_2$ | C$_2$H$_5$ | H | |
| 49 | 2-methyl-3-pyridyl | CH$_3$ | CF(CF$_3$)$_2$ | CH$_3$ | H | |
| 50 | 2-methyl-3-pyridyl | CH$_3$ | CF(CF$_3$)$_2$ | C$_2$H$_5$ | H | |
| 51 | 2-methylphenyl | CH$_3$ | CF(CF$_3$)$_2$ | C$_2$H$_5$ | H | |
| 52 | 2-methylphenyl | CH$_3$ | CF(CF$_3$)$_2$ | CH$_3$ | H | |
| 53 | 2-methylphenyl | I | CF(CF$_3$)$_2$ | I | H | |
| 54 | 2-iodophenyl | CH$_3$ | CF(CF$_3$)$_2$ | C$_2$H$_5$ | H | |
| 55 | 3-(t-butyl)-1-methyl-5-pyrazolyl | CH$_3$ | CF(CF$_3$)$_2$ | C$_2$H$_5$ | H | |
| 56 | 3-(trifluoromethyl)-2-pyridyl | CH$_3$ | CF(CF$_3$)$_2$ | CH$_3$ | H | |
| 57 | 3-(trifluoromethyl)-2-pyridyl | CH$_3$ | CF(CF$_3$)$_2$ | C$_2$H$_5$ | H | |
| 58 | 3-(trifluoromethyl)phenyl | CH$_3$ | CF(CF$_3$)$_2$ | C$_2$H$_5$ | H | |

TABLE 1-continued

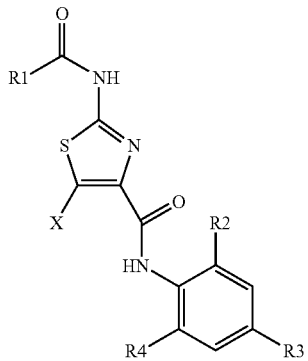

| No. | R1 | R2 | R3 | R4 | X | m. p. °C. |
|---|---|---|---|---|---|---|
| 59 | 3,4-dichlorophenyl | $CH_3$ | $CF(CF_3)_2$ | $C_2H_5$ | H | |
| 60 | 3,5-dichloro-2-pyridyl | $CH_3$ | $CF(CF_3)_2$ | $C_2H_5$ | H | |
| 61 | 3,5-dichlorophenyl | $CH_3$ | $CF(CF_3)_2$ | $C_2H_5$ | H | |
| 62 | 3-chloro-5-(trifluoromethyl)-2-pyridyl | $CH_3$ | $CF(CF_3)_2$ | $C_2H_5$ | H | |
| 63 | 3-chloro-2-thienyl | $CH_3$ | $CF(CF_3)_2$ | $CH_3$ | H | |
| 64 | 3-chloro-2-thienyl | $CH_3$ | $CF(CF_3)_2$ | $C_2H_5$ | H | |
| 65 | 3-chloro-2-pyridyl | $CH_3$ | $CF(CF_3)_2$ | $C_2H_5$ | H | |
| 66 | 3-chlorophenyl | $CH_3$ | $CF(CF_3)_2$ | $C_2H_5$ | H | |
| 67 | 3-chlorophenyl | $CH_3$ | $CF(CF_3)_2$ | $CH_3$ | H | 95-100 |
| 68 | 3-chlorophenyl | Cl | $S(O)C_2F_5$ | Cl | H | |
| 69 | 3-hydroxy-2-pyridyl | $CH_3$ | $CF(CF_3)_2$ | $C_2H_5$ | H | |
| 70 | 3-fluorophenyl | $CH_3$ | $CF(CF_3)_2$ | $C_2H_5$ | H | |
| 71 | 3-fluorophenyl | $CH_3$ | $CF(CF_3)_2$ | $CH_3$ | H | |
| 72 | 3-fluorophenyl | $CH_3$ | $CF(CF_3)_2$ | $CH_3$ | I | |
| 73 | 3-fluorophenyl | Cl | $SC_2F_5$ | Cl | H | |
| 74 | 3-bromophenyl | $CH_3$ | $CF(CF_3)_2$ | $C_2H_5$ | H | |
| 75 | 3-methylphenyl | $CH_3$ | $CF(CF_3)_2$ | $C_2H_5$ | H | |
| 76 | 3-methoxy-5-(trifluoromethyl)-2-thienyl | $CH_3$ | $CF(CF_3)_2$ | $C_2H_5$ | H | |
| 77 | 4-(trifluoromethyl)-3-pyridyl | $CH_3$ | $CF(CF_3)_2$ | $C_2H_5$ | H | |
| 78 | 4-(trifluoromethyl)-3-pyridyl | $CH_3$ | $CF(CF_3)_2$ | $CH_3$ | H | |
| 79 | 4-(trifluoromethyl)phenyl | $CH_3$ | $CF(CF_3)_2$ | $C_2H_5$ | H | |
| 80 | 4-(trifluoromethyl)phenyl | $CH_3$ | $CF(CF_3)_2$ | $CH_3$ | H | |
| 81 | 4-(trifluoromethyl)phenyl | I | $CF(CF_3)_2$ | $CH_3$ | I | |
| 82 | 4-(trifluoromethyl)phenyl | $CH_3$ | $CF(CF_3)_2$ | $CH_3$ | Me | |
| 83 | 4-(trifluoromethylsulfinyl)phenyl | $CH_3$ | $CF(CF_3)_2$ | $CH_3$ | H | |
| 84 | 4-(trifluoromethylsulfonyl)phenyl | $CH_3$ | $CF(CF_3)_2$ | $CH_3$ | H | |
| 85 | 4-(trifluoromethylthio)phenyl | $CH_3$ | $CF(CF_3)_2$ | $CH_3$ | H | |
| 86 | 4-(trifluoromethoxy)phenyl | $CH_3$ | $CF(CF_3)_2$ | $C_2H_5$ | H | |
| 87 | 4-(trifluoromethoxy)phenyl | $CH_3$ | $CF(CF_3)_2$ | $CH_3$ | H | |
| 88 | 4,6-difluoro-3-pyridyl | $CH_3$ | $CF(CF_3)_2$ | $C_2H_5$ | H | |
| 89 | 4-ethoxyphenyl | $CH_3$ | $CF(CF_3)_2$ | $CH_3$ | H | |
| 90 | 4-chlorophenyl | $CH_3$ | $CF(CF_3)_2$ | $C_2H_5$ | H | 187-189 |
| 91 | 4-chlorophenyl | $CH_3$ | $CF(CF_3)_2$ | $CH_3$ | H | 215-218 |
| 92 | 4-chlorophenyl | $CH_3$ | $CF(CF_3)_2$ | $CH(CH_3)_2$ | H | |
| 93 | 4-chlorophenyl | $C_2H_5$ | $CF(CF_3)_2$ | $C_2H_5$ | H | |
| 94 | 4-chlorophenyl | I | $CF(CF_3)_2$ | I | H | |
| 95 | 4-chlorophenyl | Cl | $S(O)C_3F_7$-n | Cl | H | |
| 96 | 4-chlorophenyl | $CH_3$ | $SCF_3$ | $CH_3$ | H | |
| 97 | 4-fluorophenyl | $CH_3$ | $CF(CF_3)_2$ | $CH_3$ | H | |
| 98 | 4-fluorophenyl | $CH_3$ | $CF(CF_3)_2$ | $C_2H_5$ | Br | |
| 99 | 4-fluorophenyl | Cl | $SCF_3$ | Cl | H | |
| 100 | 4-fluorophenyl | Br | $SCF_3$ | Br | H | |
| 101 | 4-fluorophenyl | $CH_3$ | $SC_2F_5$ | $CH_3$ | H | |
| 102 | 4-bromo-1-ethyl-3-methyl-5-pyrazolyl | $CH_3$ | $CF(CF_3)_2$ | $C_2H_5$ | H | |
| 103 | 4-bromophenyl | $CH_3$ | $CF(CF_3)_2$ | $C_2H_5$ | H | |
| 104 | 4-methyl-1,2,3-thiadiazol-5-yl | $CH_3$ | $CF(CF_3)_2$ | $C_2H_5$ | H | |
| 105 | 4-methylsulfinylphenyl | $CH_3$ | $CF(CF_3)_2$ | $CH_3$ | H | |
| 106 | 4-methylsulfonylphenyl | $CH_3$ | $CF(CF_3)_2$ | $CH_3$ | H | |
| 107 | 4-methylthiophenyl | $CH_3$ | $CF(CF_3)_2$ | $CH_3$ | H | |
| 108 | 4-methylphenyl | $CH_3$ | $CF(CF_3)_2$ | $C_2H_5$ | H | |
| 109 | 4-methoxyphenyl | $CH_3$ | $CF(CF_3)_2$ | $C_2H_5$ | H | |
| 110 | 5-chloro-1-methyl-3-(trifluoromethyl)-4-pyrazolyl | $CH_3$ | $CF(CF_3)_2$ | $C_2H_5$ | H | |
| 111 | 5-chloro-2-thienyl | $CH_3$ | $CF(CF_3)_2$ | $C_2H_5$ | H | |
| 112 | 5-chloro-3-pyridyl | $CH_3$ | $CF(CF_3)_2$ | $C_2H_5$ | H | |

TABLE 1-continued

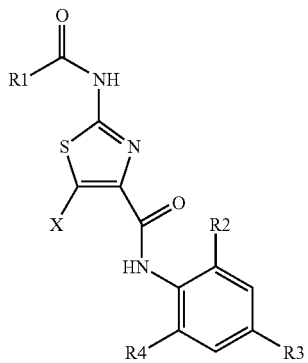

| No. | R1 | R2 | R3 | R4 | X | m.p. °C. |
|---|---|---|---|---|---|---|
| 113 | 5-methyl-4-isoxazolyl | $CH_3$ | $CF(CF_3)_2$ | $C_2H_5$ | H | |
| 114 | 6-chloro-4-(trifluoromethyl)-3-pyridyl | $CH_3$ | $CF(CF_3)_2$ | $C_2H_5$ | H | |
| 115 | 6-chloro-3-pyridyl | $CH_3$ | $CF(CF_3)_2$ | $C_2H_5$ | H | |
| 116 | 6-chloro-3-pyridyl | I | $CF(CF_3)_2$ | I | H | |
| 117 | 6-chloro-3-pyridyl | $CH_3$ | $CF(CF_3)_2$ | $CH_3$ | H | |
| 118 | 6-fluoro-3-pyridyl | $CH_3$ | $CF(CF_3)_2$ | $C_2H_5$ | H | |
| 119 | 6-fluoro-3-pyridyl | $CH_3$ | $CF(CF_3)_2$ | $CH_3$ | H | |
| 120 | 6-fluoro-3-pyridyl | Br | $CF(CF_3)_2$ | Br | H | |
| 121 | 5-isoxazolyl | $CH_3$ | $CF(CF_3)_2$ | $C_2H_5$ | H | |
| 122 | 2-thienyl | $CH_3$ | $CF(CF_3)_2$ | $C_2H_5$ | H | 202-203 |
| 123 | 2-thienyl | $CH_3$ | $CF(CF_3)_2$ | $CH_3$ | H | |
| 124 | 3-thienyl | $CH_3$ | $CF(CF_3)_2$ | $C_2H_5$ | H | |
| 125 | 2-pyridyl | $CH_3$ | $CF(CF_3)_2$ | $CH_3$ | H | |
| 126 | 2-pyridyl | $CH_3$ | $CF(CF_3)_2$ | $C_2H_5$ | H | |
| 127 | 3-pyridyl | $CH_3$ | $CF(CF_3)_2$ | $CH_3$ | H | |
| 128 | 3-pyridyl | $CH_3$ | $CF(CF_3)_2$ | $C_2H_5$ | H | |
| 129 | 4-pyridyl | $CH_3$ | $CF(CF_3)_2$ | $CH_3$ | H | |
| 130 | 4-pyridyl | $CH_3$ | $CF(CF_3)_2$ | $C_2H_5$ | H | |
| 131 | phenyl | $CH_3$ | $CF(CF_3)_2$ | $C_2H_5$ | H | |
| 132 | phenyl | $CH_3$ | $CF(CF_3)_2$ | $C_2H_5$ | Me | |
| 133 | phenyl | $CH_3$ | $C_2F_5$ | $CH_3$ | H | |
| 134 | phenyl | $CH_3$ | $CF(CF_3)_2$ | $CH_3$ | H | |
| 135 | 2-furyl | $CH_3$ | $CF(CF_3)_2$ | $C_2H_5$ | H | 191-193 |
| 136 | 2-furyl | $CH_3$ | $CF(CF_3)_2$ | $CH_3$ | H | |
| 137 | 6-chloro-5-methyl-3-pyridyl | $CH_3$ | $CF(CF_3)_2$ | $C_2H_5$ | H | |
| 138 | 4,5-dimethyl-3-pyridyl | $CH_3$ | $CF(CF_3)_2$ | $C_2H_5$ | H | |
| 139 | 4,6-dichloro-3-pyridyl | $CH_3$ | $CF(CF_3)_2$ | $C_2H_5$ | H | |
| 140 | 4-chloro-2-pyridyl | $CH_3$ | $CF(CF_3)_2$ | $C_2H_5$ | H | |
| 141 | 2-chloro-6-methylthio-4-pyridyl | $CH_3$ | $CF(CF_3)_2$ | $C_2H_5$ | H | |
| 142 | 2-hydroxy-3-pyridyl | $CH_3$ | $CF(CF_3)_2$ | $C_2H_5$ | H | |
| 143 | 2,6-difluoro-3-pyridyl | $CH_3$ | $CF(CF_3)_2$ | $C_2H_5$ | H | |
| 144 | 2-bromo-5-methyl-3-pyridyl | $CH_3$ | $CF(CF_3)_2$ | $C_2H_5$ | H | |
| 145 | 2-bromo-5-ethyl-3-pyridyl | $CH_3$ | $CF(CF_3)_2$ | $C_2H_5$ | H | |
| 146 | 5-bromo-3-pyrdiyl | $CH_3$ | $CF(CF_3)_2$ | $C_2H_5$ | H | |
| 147 | 5-(trifluoromethyl)-2-pyridyl | $CH_3$ | $CF(CF_3)_2$ | $C_2H_5$ | H | |
| 148 | 2,6-dichloro-5-fluoro-3-pyridyl | $CH_3$ | $CF(CF_3)_2$ | $C_2H_5$ | H | |
| 149 | 3,5-dichloro-4-pyridyl | $CH_3$ | $CF(CF_3)_2$ | $C_2H_5$ | H | |
| 150 | 3-chloro-4-pyridyl | $CH_3$ | $CF(CF_3)_2$ | $C_2H_5$ | H | |
| 151 | 5-chloro-2-pyridyl | $CH_3$ | $CF(CF_3)_2$ | $C_2H_5$ | H | |
| 152 | 6-chloro-2-pyridyl | $CH_3$ | $CF(CF_3)_2$ | $C_2H_5$ | H | |
| 153 | 2-fluorophenyl | Br | $CF(CF_3)_2$ | Br | H | |
| 154 | 4-chlorophenyl | Br | $CF(CF_3)_2$ | Br | H | |
| 155 | 2,6-difluorophenyl | Br | $CF(CF_3)_2$ | Br | H | 183-188 |
| 156 | 2-chloro-3-pyridyl | I | $CF(CF_3)_2$ | I | H | |
| 157 | 2-fluoro-3-pyridyl | Br | $CF(CF_3)_2$ | Br | H | |
| 158 | 2-fluorophenyl | $CH_3$ | $CF(CF_3)_2$ | $CH_3$ | Cl | 221 |

BIOLOGICAL TEST EXAMPLE 1

Test for Embryos of *Spodoptera litura*

Preparation of Sample Drug Solution

| | |
|---|---|
| Solvent: dimethyl formamide | 3 parts by weight |
| Emulsifier: polyoxyethylene alkylphenyl ether | 1 part by weight |

1 Part by weight of the active compound was mixed with the above-mentioned amount of a solvent containing the above-mentioned amount of emulsifier in order to prepare the formulation of an appropriate active compound, and the mixture was diluted with water to a predetermined concentration.

Test Method

The leaves of sweet potato were immersed in a sample drug solution which was diluted with water to a predetermined concentration and charged in a petri dish with a diameter of 9 cm after drying the drug solution. 10 of embryos with 3 instar of *Spodoptera litura* were dropped thereto, the petri dish was placed in a constant temperature chamber at 25° C., the leaves of sweet potato were additionally added after 2 days and 4 days and the number of dead embryos was examined after 7 days to calculate an insecticidal rate.

In the present test, the result of 2 petri dishes per one partition was averaged.

Test Result

In the above-mentioned Biological Test Example 1, the compounds of the compound Nos. 21, 24, 34, 35, 41, 42, 67, 90, 91, 155 and 158 as typical Examples exhibited the effect of pest control with an insecticidal rate of 100% at an effective ingredient concentration of 20 ppm.

Biological Test Example 2

Test for *Tetranychus urticae* (Spray Test)

Test Method 50 to 100 of adult insects of *Tetranychus urticae* were inoculated on the leaves of butter bean at the evolution period of 2 true leaves which were cultivated in a pot with a diameter of 6 cm. An adequate amount of an aqueous diluted solution with a predetermined concentration of the active compound prepared as above was sprayed after 1 day using a spray gun. After the spray, it was placed in a greenhouse and an acaricidal rate was calculated after 7 days.

Test Result

The compounds of the compound Nos. 67, 90 and 155 as typical Examples exhibited the effect of pest control with an insecticidal rate of 98% or more at an effective ingredient concentration of 500 ppm.

FORMULATION EXAMPLE 1

Granules 25 parts of water was added to a mixture of 10 parts of the compound No. 21 of the present invention, 30 parts of bentonite (montmorillonite), 58 parts of talc and 2 parts of lignin sulfonate. It was adequately kneaded and granulated to granules with 10 to 40 meshes by an extruding granulator and they were dried at 40 to 50° C. to prepare granules.

FORMULATION EXAMPLE 2

Granules 95 parts of clay mineral granules having a particle diameter distribution of a range of 0.2 to 2 mm were charged in a rotary mixer, 5 parts of the compound No. 21 of the present invention was sprayed together with a liquid diluent under rotation to uniformly wet them and then they were dried at 40 to 506° C. to prepare granules.

FORMULATION EXAMPLE 3

Emulsion 30 parts of the compound No. 21 of the present invention, 55 parts of xylene, 8 parts of polyoxyethylene alkylphenyl ether and 7 parts of calcium alkylbenzene sulfonate were mixed by stirring to prepare emulsion.

FORMULATION EXAMPLE 4

Water-Dispersible Powder 15 parts of the compound No. 21 of the present invention, 80 parts of a mixture of white carbon (amorphous silicon oxide fine powder containing water) and powdery clay (1:5), 2 parts of sodium alkylbenzene sulfonate and 3 parts of the condensate of formalin with sodium alkylnaphthalene sulfonate were mixed by pulverization to prepare water-dispersible powder.

FORMULATION EXAMPLE 5

Water-Dispersible Granules 20 parts of the compound No. 21 of the present invention, 30 parts of sodium lignin sulfonate, 15 parts of bentonite and 35 parts of calcined diatomaceous earth powder were adequately mixed, water was added thereto and the mixture was extruded with a screen of 0.3 mm and dried to prepare water-dispersible granules.

The invention claimed is:

1. A 2-Acylaminothiazole-4-carboxamide of the formula (I)

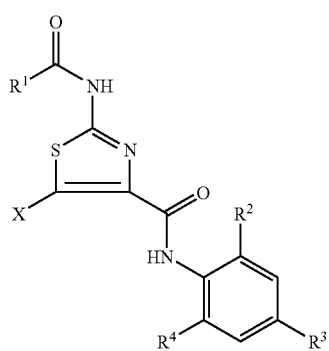

wherein $R^1$ represents phenyl which may be optionally substituted, or a 5- or 6-membered heterocyclic group comprising at least one hetero atom selected from the group consisting of N, O and S which may be optionally substituted, $R^2$ represents halogen, $C_{1-6}$ alkyl or $C_{1-6}$ haloalkyl, R³ represents C₁₋₆ haloalkyl, C₁₋₆ haloalkoxy, C₁₋₆ haloalkylthio, C₁₋₆ haloalkylsulfinyl or C₁₋₆ haloalkylsulfonyl, R⁴ represents halogen, C₁₋₆ alkyl or C₁₋₆ haloalkyl, and X represents hydrogen, halogen, C₁₋₆ alkyl or C₁₋₆ haloalkyl.

2. A carboxamide according to claim 1, wherein R¹ represents phenyl which may be optionally substituted with at least one selected arbitrarily from the group consisting of C₁₋₆ alkyl, C₁₋₆ alkoxy, C₁₋₆ alkylthio, C₁₋₆ alkylsulfinyl, C₁₋₆ alkylsulfonyl, C₁₋₆ haloalkyl, C₁₋₆ haloalkoxy, C₁₋₆ haloalkylthio, C₁₋₆ haloalkylsulfinyl or C₁₋₆ haloalkylsulfonyl, nitro, hydroxy and halogen, or a 5- or 6-membered heterocyclic group comprising at least one hetero atom selected from the group consisting of N, O and S which may be optionally substituted with at least one selected arbitrarily from the group consisting of C₁₋₆ alkyl, C₁₋₆ alkoxy, C₁₋₆ alkylthio, C₁₋₆ alkylsulfinyl, C₁₋₆ alkylsulfonyl, C₁₋₆ haloalkyl, C₁₋₆ haloalkoxy, C₁₋₆ haloalkylthio, C₁₋₆ haloalkylsulfinyl or C₁₋₆ haloalkylsulfonyl, nitro, hydroxy and halogen, R² represents halogen, C₁₋₄ alkyl or C₁₋₄ haloalkyl, R³ represents C₁₋₄ haloalkyl, C₁₋₄ haloalkoxy, C₁₋₄ haloalkylthio, C₁₋₄ haloalkylsulfinyl or C₁₋₄ haloalkylsulfonyl, R⁴ represents halogen, C₁₋₄ alkyl or C₁₋₄ haloalkyl, and X represents hydrogen, halogen, C₁₋₄ alkyl or C₁₋₄ haloalkyl.

3. A carboxamide according to claim 1, wherein R¹ represents phenyl which may be optionally substituted with at least one selected arbitrarily from a group consisting of C₁₋₄ alkyl, C₁₋₄ alkoxy, C₁₋₄ alkylthio, C₁₋₄ alkylsulfinyl, C₁₋₄ alkylsulfonyl, C₁₋₄ haloalkyl, C₁₋₄ haloalkoxy, C₁₋₄ haloalkylthio, C₁₋₄ haloalkylsulfinyl or C₁₋₄ haloalkylsulfonyl, nitro, hydroxy and halogen, or pyridyl, pyrazolyl, thienyl, furyl, isooxazolyl or thiadiazolyl which may be optionally substituted with at least one selected arbitrarily from a group consisting of C₁₋₄ alkyl, C₁₋₄ alkoxy, C₁₋₄ alkylthio, C₁₋₄ alkylsulfinyl, C₁₋₄ alkylsulfonyl, C₁₋₄ haloalkyl, C₁₋₄ haloalkoxy, C₁₋₄ haloalkylthio, C₁₋₄ haloalkylsulfinyl or C₁₋₄ haloalkylsulfonyl, nitro, hydroxy and halogen, R² represents fluoro, chloro, bromo, iodo, methyl, ethyl, propyl, butyl, trifluoromethyl or perfluoroethyl, R³ represents C₁₋₄ haloalkyl, C₁₋₄ haloalkoxy, C₁₋₄ haloalkylthio, C₁₋₄ haloalkylsulfinyl or C₁₋₄ haloalkylsulfonyl, R⁴ represents fluoro, chloro, bromo, iodo, methyl, ethyl, propyl, butyl, trifluoromethyl or perfluoroethyl, and X represents hydrogen, fluoro, chloro, bromo, iodo or methyl.

4. A carboxamide according to claim 1, wherein

R¹ represents phenyl which may be optionally substituted with at least one selected arbitrarily from chloro and fluoro or R¹ represents thienyl or furyl, R² represents bromo, iodo, methyl, R³ represents C₁₋₄ haloalkyl, R⁴ represents bromo, iodo, methyl, ethyl, and X represents hydrogen or chloro.

5. A process for the preparation of a carboxamide of formula (I) according to claim 1, comprising (a) reacting a compound of formula (II)

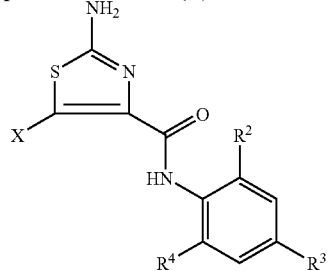

(II)

with a compound of formula (III)

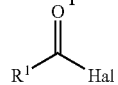

(III)

wherein Hal represents halogen, in the presence of an inert solvent, and if appropriate, in the presence of a base and/or a phase transfer catalyst, and/or (b) reacting a compound of formula (IV)

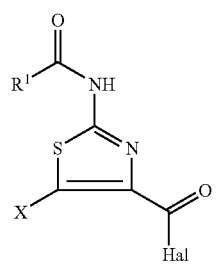

(IV)

with a compound of formula (V)

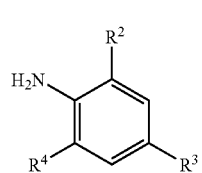

(V)

in the presence of an inert solvent, and if appropriate, in the presence of a base and/or a phase transfer catalyst.

6. An Insecticidal composition, comprising at least one carboxamide of formula (I) according to claim 1.

7. A process for combating insects, comprising allowing a carboxamide of formula (I) according to claim 1 to act on harmful insects and/or a habitat.

8. A method for combating harmful insects comprising employing a carboxamide according to claim 1.

9. A process for the preparation of an insecticidal composition, comprising mixing a carboxamide compound of formula (I) according to claim 1 with an extender and/or a surface active agent.

10. A compound of a formula (II)

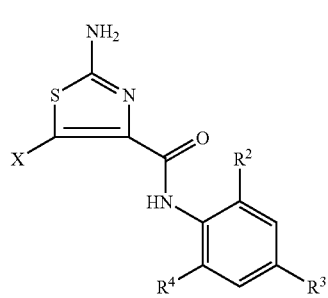

(II)

Wherein $R^2$ represents halogen, $C_{1-6}$ alkyl or $C_{1-6}$ haloalkyl,
$R^3$ represents $C_{1-6}$ haloalkyl, $C_{1-6}$ haloalkoxy, $C_{1-6}$ haloalkylthio, $C_{1-6}$ haloalkylsulfinyl or $C_{1-6}$ haloalkylsulfonyl,
$R^4$ represents halogen, $C_{1-6}$ alkyl or $C_{1-6}$ haloalkyl, and
X represents hydrogen, halogen, $C_{1-6}$ alkyl or $C_{1-6}$ haloalkyl.

11. A compound of formula (VI)

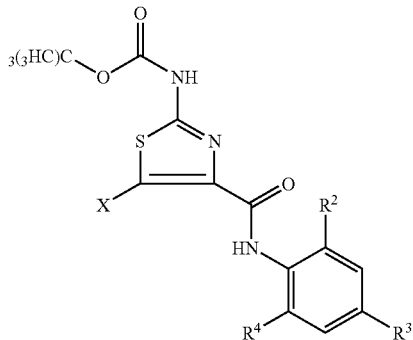

(VI)

Wherein $R^2$ represents halogen, $C_{1-6}$ alkyl or $C_{1-6}$ haloalkyl,
$R^3$ represents $C_{1-6}$ haloalkyl, $C_{1-6}$ haloalkoxy, $C_{1-6}$ haloalkylthio, $C_{1-6}$ haloalkylsulfinyl or $C_{1-6}$ haloalkylsulfonyl,
$R^4$ represents halogen, $C_{1-6}$ alkyl or $C_{1-6}$ haloalkyl, and
X represents hydrogen, halogen, $C_{1-6}$ alkyl or $C_{1-6}$ haloalkyl.

12. A composition according to claim 6 for the treatment of seeds.

13. A composition according to claim 6 adapted for treatment of transgenic plants.

14. A composition according to claim 6 adapted for the treatment of seeds of transgenic plants.

15. A method for treating seeds comprising treating the seeds with a composition according to claim 6.

16. A method for treating transgenic plants comprising applying a composition according to claim 6.

17. A method for treating the seeds of transgenic plants comprising treating the seeds of transgenic plants with a composition according to claim 6.

18. A seed treated according to the method of claim 15.

* * * * *